United States Patent
Kudoh et al.

(10) Patent No.: US 10,166,324 B2
(45) Date of Patent: Jan. 1, 2019

(54) METHODS AND SYSTEM FOR TREATING ARTHRITIS

(71) Applicant: TERUMO KABUSHIKI KAISHA, Shibuya-ku, Tokyo (JP)

(72) Inventors: Takeshi Kudoh, Hiratsuka (JP);
Shinsuke Nakaya, Fujinomiya (JP);
Tomohiro Sudo, Fujinomiya (JP);
Hideto Nagata, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/423,779

(22) Filed: Feb. 3, 2017

(65) Prior Publication Data

US 2017/0224906 A1    Aug. 10, 2017

(30) Foreign Application Priority Data

Feb. 8, 2016    (JP) .................. 2016-022269

(51) Int. Cl.
*A61M 3/02* (2006.01)
*A61M 1/00* (2006.01)

(52) U.S. Cl.
CPC ........ *A61M 3/0279* (2013.01); *A61M 1/0064* (2013.01); *A61M 3/0283* (2013.01); *A61M 3/0258* (2013.01); *A61M 2202/06* (2013.01)

(58) Field of Classification Search
CPC .............. A61M 3/0279; A61M 3/0283; A61M 3/0258; A61M 1/0064; A61M 2202/06
See application file for complete search history.

(56) References Cited

U.S. PATENT DOCUMENTS

| | | | |
|---|---|---|---|
| 2012/0165787 A1* | 6/2012 | Hwang | A61K 31/728 604/518 |
| 2015/0032046 A1* | 1/2015 | Deborski | A61N 7/00 604/21 |

FOREIGN PATENT DOCUMENTS

| | | |
|---|---|---|
| JP | 2009-529992 | 8/2009 |
| WO | WO 2007/107327 | 9/2007 |

* cited by examiner

*Primary Examiner* — Theodore Stigell
(74) *Attorney, Agent, or Firm* — Jason H. Vick; Sheridan Ross, PC

(57) ABSTRACT

Provided is an arthritis treatment method and an arthritis treatment system which can be effective for the short-term attainment of a pain relief effect. An arthritis treatment method includes an instrument introducing step of causing at least one instrument having a tubular shape to communicate with a lesion area in which crystal-induced arthritis occurs, and a treatment step of removing a causative agent of the crystal-induced arthritis from the lesion area by perfusion and discharge of a lavage fluid through the instrument.

5 Claims, 10 Drawing Sheets

METHODS AND SYSTEM FOR TREATING ARTHRITIS

CROSS REFERENCE TO RELATED APPLICATION

The present application claims the benefit of priority, under 35 U.S.C. § 119(e), to Japanese Patent Application No. 2016-022269, filed Feb. 8, 2016, entitled "Arthritis Treatment Method and Arthritis Treatment System," the entire disclosure of which is hereby incorporated herein by reference, in its entirety, for all that it teaches and for all purposes.

TECHNICAL FIELD

The present disclosure relates to an arthritis treatment method and an arthritis treatment system.

BACKGROUND

In recent years, gout, which is a typical example of crystal-induced arthritis, has been increasing year by year, and even the number of conscious patients has reached the level of one million.

Gout is developed by causative agents, such as uric acid crystals depositing in the joint and chemical substances released by phagocytosis by white blood cells or the like of those crystals, and causes severe pain, swelling, or fever.

Treatment for gout typically includes the administration of a drug, but the perfusion of a drug into a lesion area as in a treatment for cancer discussed in, for example, the treatment described in Japanese Patent Application No. JP-T-2009-529992, the entire contents of which are hereby incorporated herein by reference for all that it teaches and for all purposes, has not been established.

SUMMARY

Technical Problem

When an attack of gout (severe pain) has occurred, the currently available way to deal with the attack is only to keep the patient at rest for about one day to seven days until the attack ceases by the administration of a drug, so that the patient has to bear severe pain for hours.

Therefore, the present disclosure addresses the above-mentioned problems, and provides an arthritis treatment method and an arthritis treatment system which can be effective for the short-term attainment of a pain relief effect.

Solution to the Problem

An arthritis treatment method according to the embodiments herein includes an instrument introducing step of causing at least one instrument having a tubular shape to communicate with a lesion area in which crystal-induced arthritis occurs, and a treatment step of removing a causative agent of the crystal-induced arthritis from the lesion area by perfusion and discharge of a lavage fluid through the instrument.

An arthritis treatment system according to the embodiments herein is used for treatment of crystal-induced arthritis and includes a lavage fluid supply unit configured to pressurize and supply a lavage fluid, and at least one instrument having a tubular shape configured to enable communication between the lavage fluid supply unit and a lesion area and communication between the lesion area and a body outside.

Advantages

The arthritis treatment method and the arthritis treatment system configured as described above, allow a causative agent in the lesion area to be removed, and a short-term attainment of pain relief can be achieved.

DETAILED DESCRIPTION

Figure 1:
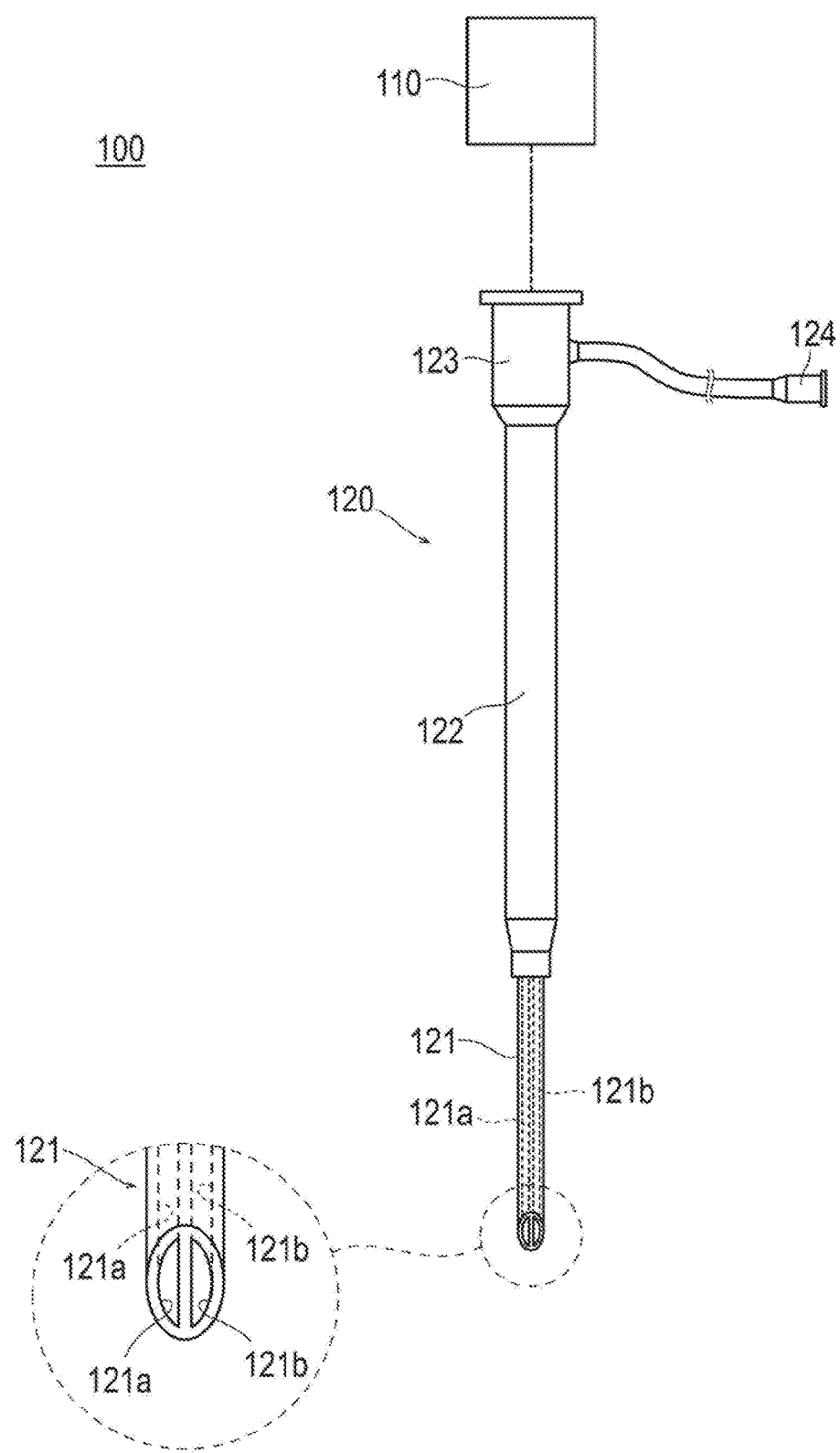
FIG. 1 is a diagram illustrating a schematic configuration of an embodiment of an arthritis treatment system.

Hereinafter, embodiments will be described with reference to the accompanying drawings. Moreover, dimensional ratios illustrated in the drawings may be exaggerated for the purpose of illustration and may be different from the actual ratios.

As illustrated in FIG. 1, an arthritis treatment system 100 includes a lavage fluid supply unit 110 and a puncture instrument 120 (a single instrument having a tubular shape).

The lavage fluid supply unit 110 pressurizes and supplies a lavage fluid to the puncture instrument 120. The lavage fluid is, for example, physiological salt solution, Riger's solution, or Hanks' solution, but is not specifically limited as long as it is a liquid having biocompatibility.

The lavage fluid supply unit 110, which can be any one capable of pressurizing and supplying a lavage fluid to the puncture instrument 120, is, for example, a syringe, but is not limited to that. The lavage fluid supply unit 110 can include, for example, a storage portion in which a lavage fluid is accumulated, and a pump which pressurizes the lavage fluid from the storage portion to the puncture instrument 120.

The puncture instrument 120 includes a needle 121, a main body portion 122, a first hub portion 123, and a second hub portion 124.

The needle 121 has a tubular shape in which two lumens 121*a* and 121*b* are formed. The needle 121 has an acute distal end inclined with respect to the axial direction. The lumens 121*a* and 121*b* penetrate through the distal end of the needle 121.

The main body portion 122 is a shaft-like member, one end of which is provided with the needle 121 and the other end of which is provided with the first hub portion 123. The lumens 121*a* and 121*b* extend to the first hub portion 123 through the main body portion 122.

The first hub portion 123 is freely connectable to the lavage fluid supply unit 110. Moreover, the second hub portion 124 branches off from the first hub portion 123.

The lumen 121*a* communicates with the lavage fluid supply unit 110 through the main body portion 122 and the first hub portion 123. The lavage fluid, which is pressurized and supplied from the lavage fluid supply unit 110, is released from the distal end of the needle 121 through the lumen 121*a*. The lumen 121*b* communicates with an external portion through the main body portion 122, the first hub portion 123, and the second hub portion 124. The lumen 121*a* and the lumen 121*b* are separated from each other and do not communicate with each other.

By way of example, the following arthritis treatment method is described on the assumption that gout has occurred in a joint of the foot.

Figure 2:
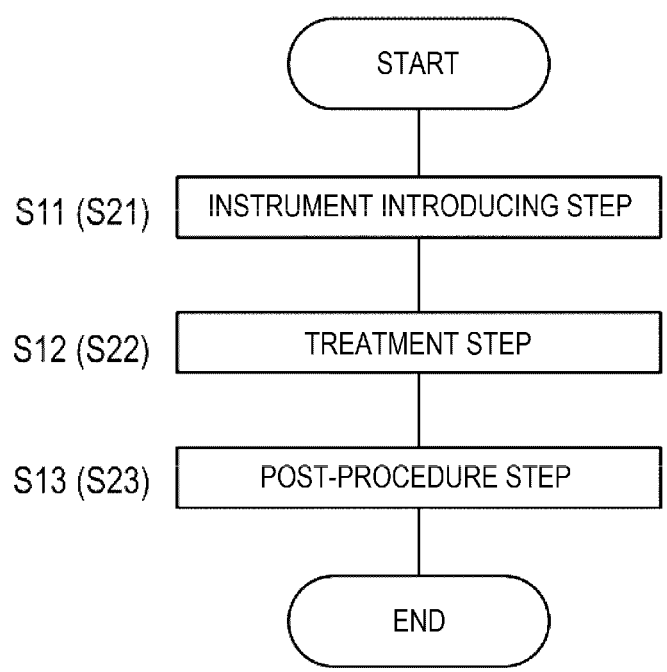
FIG. 2 is a flowchart of an embodiment of an arthritis treatment method.

As illustrated in FIG. 2, the arthritis treatment method may include an instrument introducing step S11, a treatment step S12, and a post-procedure step S13. The arthritis treatment method may be performed using the above-described arthritis treatment system 100, and is desirably performed when an attack of gout (severe pain) occurs.

If treatment is provided during an asymptomatic state in which no attack of gout occurs, an attack may be induced by treatment. However, providing treatment during the occurrence of an attack enables preventing such an induction.

Figure 3:
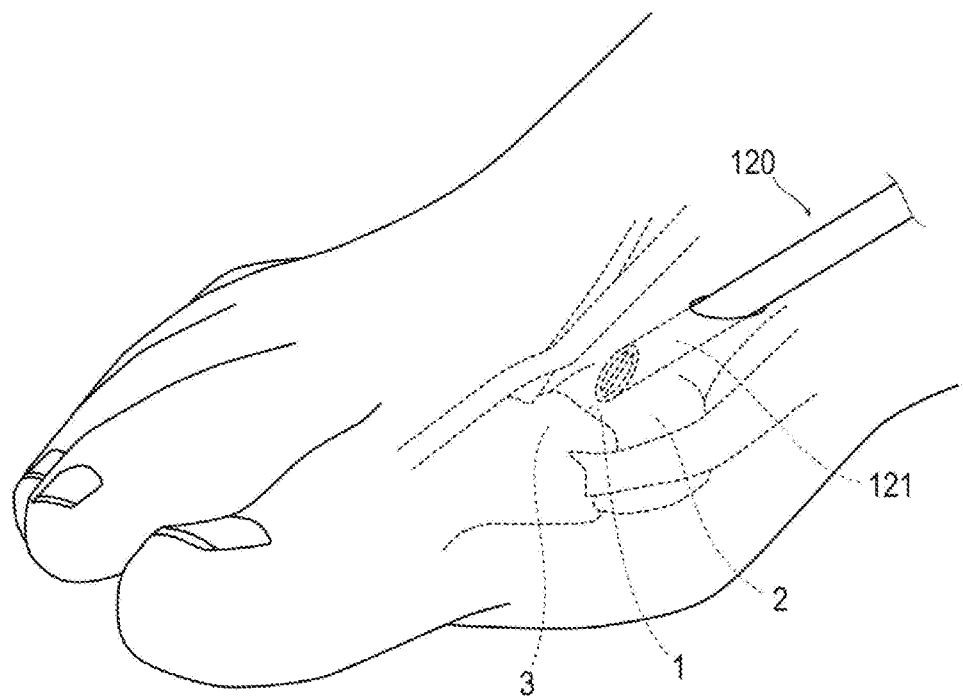
FIG. 3 is a diagram illustrating an embodiment of a condition in which a lesion area is punctured with a puncture instrument.

As illustrated in FIG. 3, in the instrument introducing step S11, the operator causes the puncture instrument 120 to communicate with a lesion area 1 in which gout has occurred. In some embodiments, the lesion area 1 may be the joint between the first metatarsal bone 2 and the proximal phalanx 3. The operator inserts the needle 121 toward the lesion area 1 to cause the puncture instrument 120 to communicate with the lesion area 1.

Then, in the treatment step S12, the perfusion and discharge of the lavage fluid through the puncture instrument 120 cause a causative agent of gout to be removed from the lesion area 1.

Figure 4:
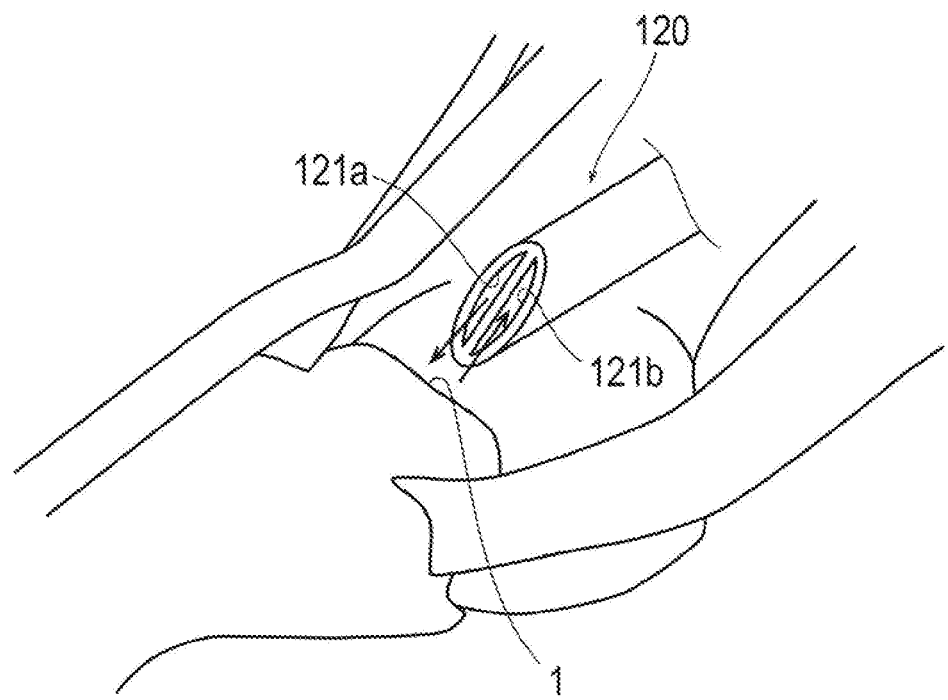
FIG. 4 is a diagram illustrating an embodiment of perfusion and discharge of a lavage fluid through the puncture instrument.

As illustrated in FIG. 4, the lavage fluid is ejected from the lumen 121*a* while being weakly pressurized and is then perfused through the lesion area 1. The term "perfusing" refers to forcing a liquid to flow over or through a specific site of the body.

Since the weakly-pressurized injection of the lavage fluid increases the pressure in the vicinity of the lesion area 1, the lavage fluid containing causative agents of the lesion area 1 flows into the lumen 121*b* as an effluent, and may then be directly discharged to the body outside through the lumen 121*b*. As a result, the causative agents are removed from the lesion area 1. The effluent discharged to the body outside can be collected using a collection unit such as a beaker.

The causative agents of the lesion area 1 are, for example, crystals of uric acid salt (free uric acid crystals) separating around the joint and chemical substances released by phagocytosis by white blood cells or the like of those crystals. After removal of the causative agents, the post-procedure step S13 is performed.

Figure 5:
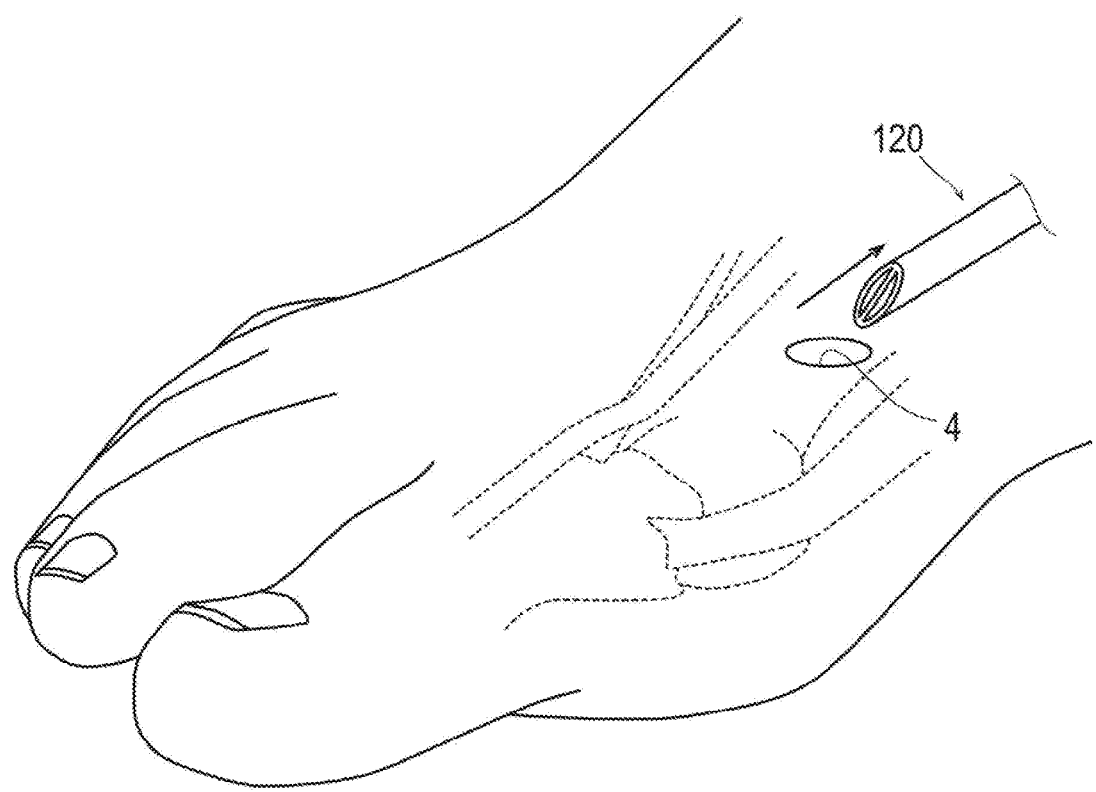
FIG. 5 is a diagram illustrating an embodiment of extraction of the puncture instrument.

As illustrated in FIG. 5, in the post-procedure step S13, the operator extracts the puncture instrument 120 from the foot, and then closes a wound 4 formed by the puncture instrument 120 using, for example, sutures.

Next, the function effect of the treatment is described in accordance with embodiments of the present disclosure.

In the case of suppressing an attack of gout by the administration of a drug, unlike the embodiments described in the present disclosure, the patient has to bear severe pain for hours until the drug takes effect. On the other hand, according to the embodiments described in the present disclosure, since the causative agents are removed by the perfusion and discharge of a lavage fluid and the lesion area 1 is directly treated, the short-term attainment of a pain relief effect can be expected.

Since the treatment described herein may be performed by the puncture instrument 120, having a tubular shape, being caused to communicate with the lesion area 1, it is not necessary to make a large incision in the lesion area 1, and the burden on the patient can be reduced.

In particular, since the arthritis treatment system 100 described herein may include a single puncture instrument 120 and treatment may be performed through the single puncture instrument 120, only a single small wound 4 may be formed, so that the burden on the patient can be effectively reduced.

Moreover, applying the presently disclosed embodiments to gout, with which the number of patients is especially large in crystal-induced arthritis caused by crystals depositing in the joint, enables relieving the burdens on a larger number of patients.

Figure 6:
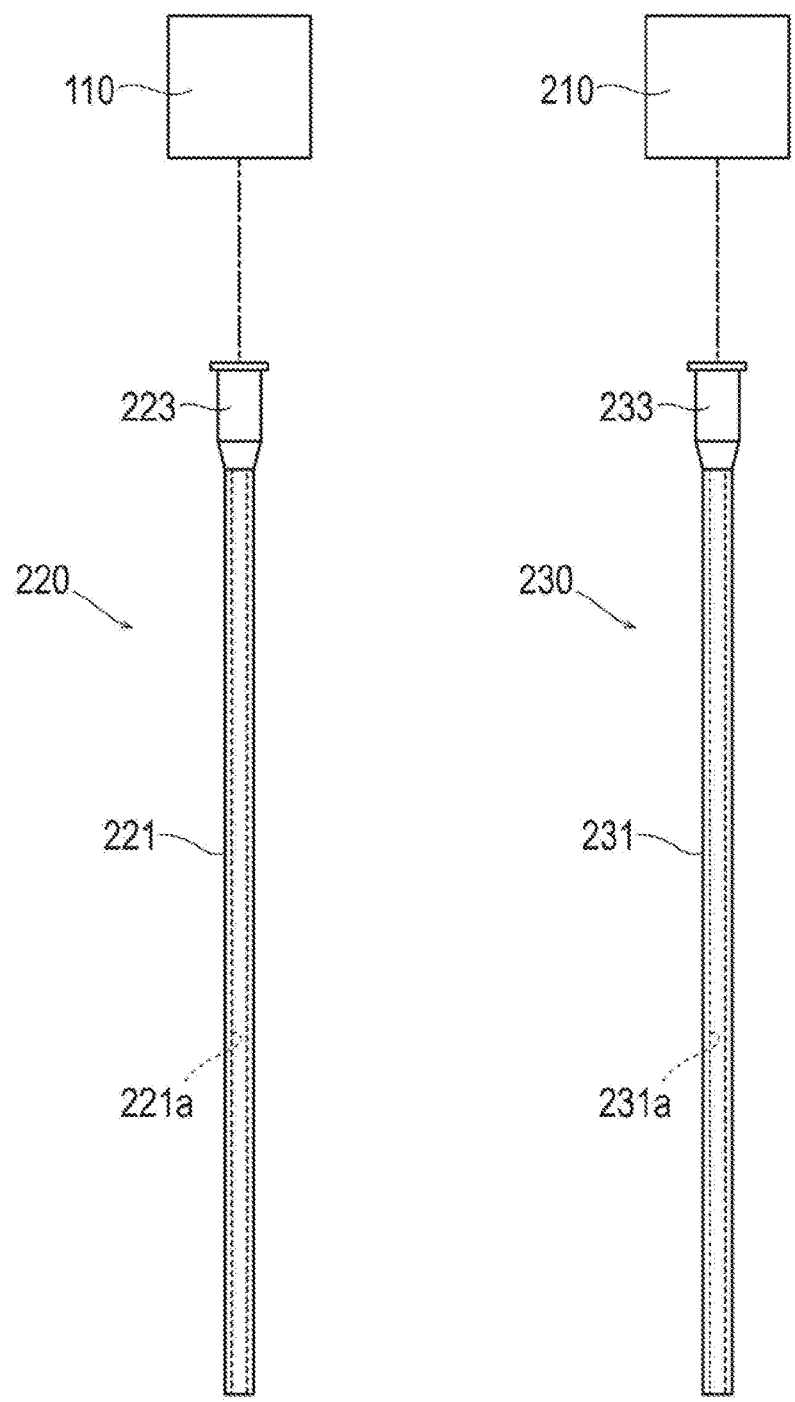
FIG. 6 is a diagram illustrating a schematic configuration of an embodiment of an arthritis treatment system.

As illustrated in FIG. 6, an arthritis treatment system 200 may include a lavage fluid supply unit 110, an aspiration unit 210, and two catheter 220 and 230 (two instruments having a tubular shape).

The lavage fluid supply unit 110 described in conjunction with FIG. 6 may be similar to, or the same as, the lavage fluid supply unit 110 described above, as such the same reference numeral is used, and any redundant description thereof is omitted. The aspiration unit 210, which can be any unit capable of aspirating air in the catheter 230 and a lavage fluid that has been used to lavage the target lesion, is, for example, a syringe or a pump, but is not limited to those.

The catheter 220 includes a main body portion 221 and a hub portion 223.

The main body portion 221 is a tubular member having flexibility in which a single lumen 221*a* is formed. The lumen 221*a* penetrates through the main body portion 221 in the axial direction thereof.

The hub portion 223, which is provided at one end of the main body portion 221, communicates with a lumen 221*a*. The hub portion 223 is freely connectable to the lavage fluid supply unit 110. The lumen 221*a* communicates with the lavage fluid supply unit 110 through the hub portion 223. The lavage fluid pressurized and supplied from the lavage fluid supply unit 110 is ejected from the distal end of the main body portion 221 through the lumen 221*a*.

The catheter 230 is similar in configuration to the catheter 220, but may be different from the catheter 220 in that the catheter 230 may be connected to the aspiration unit 210. The configuration of the main body portion 231 is similar to the configuration of the main body portion 221. The configuration of the hub portion 233 is approximately similar to that of the hub portion 223, but is different in that the hub portion 223 may be freely connectable to the aspiration unit 210.

The lumen 231a formed in the main body portion 231 penetrates through the main body portion 231 in the axial direction thereof, and communicates with the aspiration unit 210 through the hub portion 233. The aspiration unit 210, which is connected the hub portion 233, aspirates air in the lumen 231a and a lavage fluid that has been used to lavage the target lesion.

Next, an embodiment of an arthritis treatment method is described.

The arthritis treatment method may include three steps S21 to S23 (also illustrated in FIG. 2), as described above, however, in some embodiments, a specific procedure performed in each step may be different from that previously described.

Figure 7:
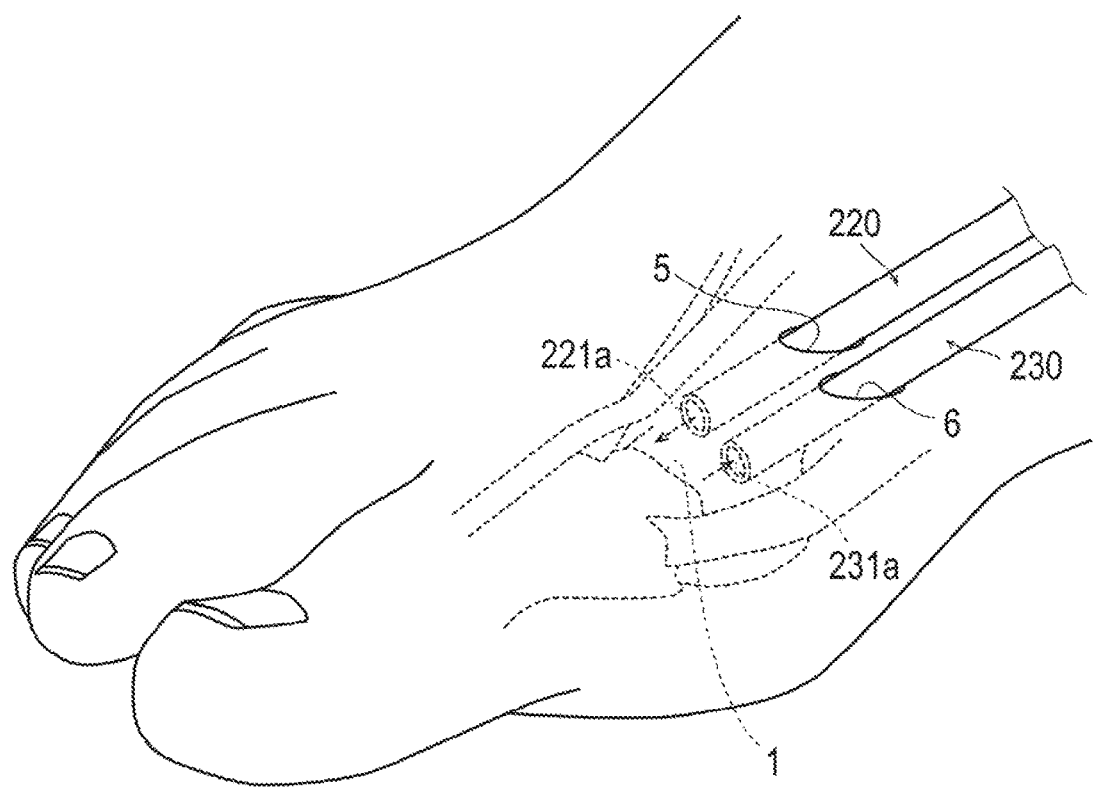
FIG. 7 is a diagram illustrating an embodiment of perfusion and discharge of a lavage fluid through two catheters.

As illustrated in FIG. 7, in the instrument introducing step S21, the operator causes the two catheters 220 and 230 to communicate with a lesion area 1. The lesion area 1 is similar to the lesion area 1 previously described.

The operator forms two small wounds 5 and 6 in the vicinity of the lesion area 1, and then causes the catheters 220 and 230 to communicate with the lesion area 1 through the wounds 5 and 6.

Then, in the treatment step S22, the perfusion of the lavage fluid through one catheter 220 and the discharge of the lavage fluid through the other catheter 230 cause a causative agent of gout to be removed from the lesion area 1.

The operator alternately performs the perfusion of the lavage fluid through the catheter 220 and the discharge of the lavage fluid through the catheter 230, but it should be apricated that the perfusion and discharge may be simultaneously performed by the operator.

The lavage fluid is ejected from the lumen 221a while being weakly pressurized and is then perfused through the lesion area 1. The lavage fluid containing causative agents of the lesion area 1 is aspirated through the lumen 231a, and is then discharged to the aspiration unit 210 outside the body as an effluent. The aspiration unit 210 can also communicate with a collection unit, such as a tank which accumulates the effluent, thus enabling collecting the effluent.

After the perfusion and discharge of the lavage fluid are alternately repeated a plurality of times, the post-procedure step S23 is performed. In the post-procedure step S23, the operator extracts the catheters 220 and 230 from the foot, and then closes the wound 5 and 6 using, for example, sutures.

Next, the function effect of the treatment is described in accordance with embodiments of the present disclosure.

The arthritis treatment system 200 may include two catheters 220 and 230, and separately uses the catheters 220 and 230 for the perfusion and discharge of the lavage fluid, respectively. This enables the lavage fluid and the effluent to flow through the lumens 221a and 231a, which are larger in inside diameter, respectively, thus more improving the perfusion function and discharge function for the lavage fluid.

Furthermore, embodiments of the present disclosure may include a structure similar to that previously described, and as such the function effect provided by such a structure may be similar to the previously described function effect.

Figure 8:
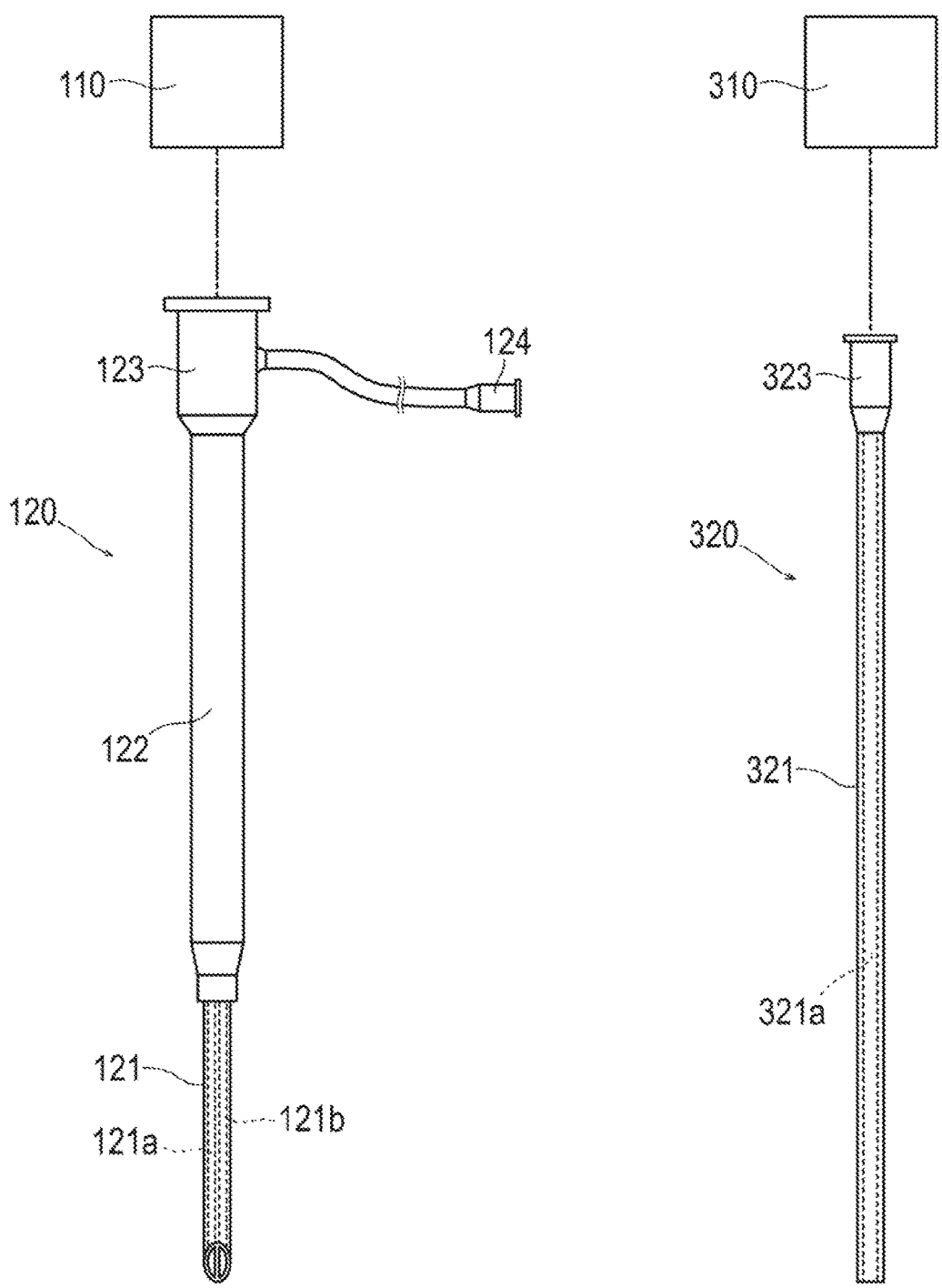
FIG. 8 is a diagram illustrating a schematic configuration of an embodiment of an arthritis treatment system.

As illustrated in FIG. 8, an arthritis treatment system 300 may include a lavage fluid supply unit 110, a gel supply unit 310, a puncture instrument 120, and a catheter 320 (an instrument having a tubular shape communicating with the gel supply unit).

Since the lavage fluid supply unit 110 and the puncture instrument 120 described herein may be similar to, or the same as, those described above, as such the respective same reference numerals may be used, and any redundant description thereof is omitted.

The gel supply unit 310 pressurizes and supplies a gel-like material to the catheter 320. The gel-like material includes, for example, a steroidal drug, such as triamcinolone acetonide and dexamethasone sodium phosphate, or an anti-inflammatory drug, such as methotrexate and aspirin, and a contrast agent, but is not limited to those. Moreover, the gel-like material desirably has biodegradability.

The gel supply unit 310, which can be any one capable of pressurizing and supplying a gel-like material to the catheter 320, is, for example, a syringe, but is not limited to that. The gel supply unit 310 can include, for example, a storage portion in which a gel-like material is accumulated, and a pump which pressurizes the gel-like material from the storage portion to the catheter 320.

The catheter 320 includes a main body portion 321 and a hub portion 323.

The main body portion 321 is a tubular member having flexibility in which a lumen 321a is formed. The lumen 321a penetrates through the main body portion 321 in the axial direction thereof.

The hub portion 323, which is provided at one end of the main body portion 321, communicates with a lumen 321a. The hub portion 323 is freely connectable to the gel supply unit 310. The lumen 321a communicates with the gel supply unit 310 through the hub portion 323. The gel-like material pressurized and supplied from the gel supply unit 310 is ejected from the distal end of the main body portion 321 through the lumen 321a.

Next, an embodiment of an arthritis treatment method is described.

Figure 9:
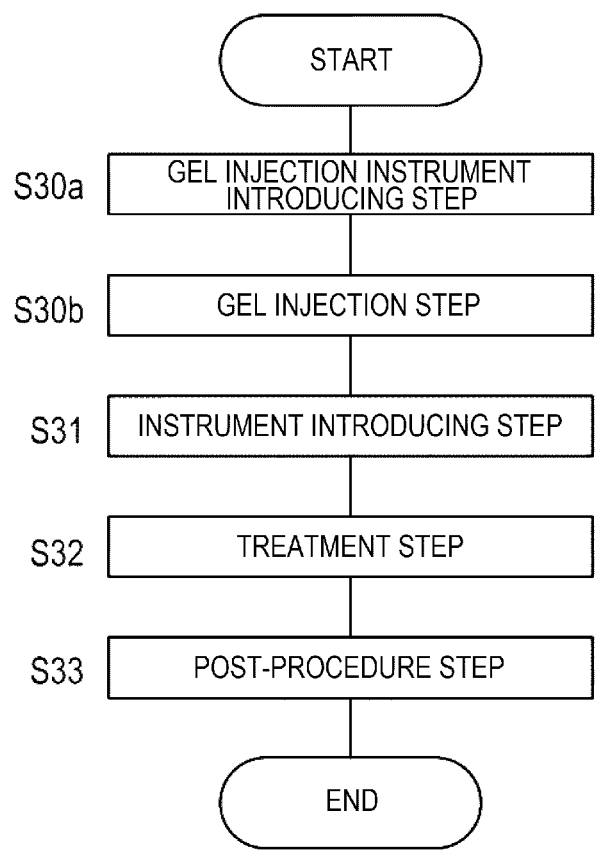
FIG. 9 is a flowchart of an embodiment of an arthritis treatment method.

As illustrated in FIG. 9, the arthritis treatment method may include a gel injection instrument introducing step S30a, a gel injection step S30b, an instrument introducing step S31, a treatment step S32, and a post-procedure step S33.

The arthritis treatment method may be different from embodiments previously described in that the gel injection instrument introducing step S30a and the gel injection step S30b may be provided ahead of the instrument introducing step S31, but the other steps S31 to S33 are approximately similar to the steps S11 to S13, described at least in conjunction with FIG. 2, respectively.

Figure 10:
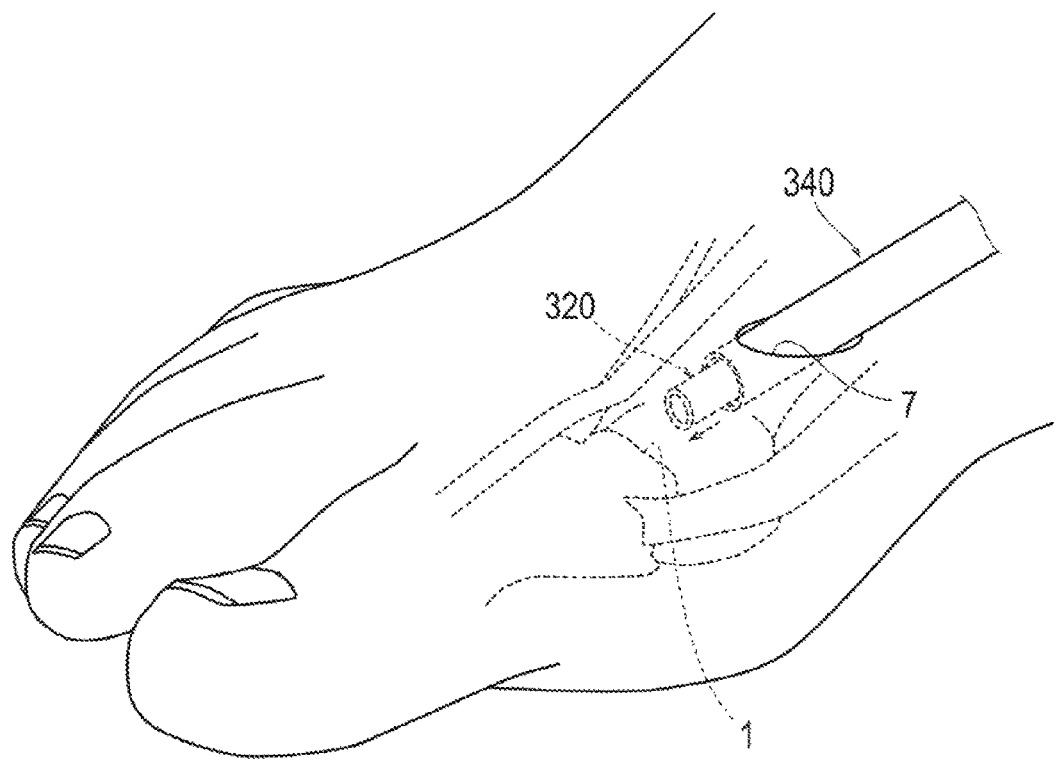
FIG. 10 is a diagram illustrating communication of an embodiment of a catheter with a lesion area.

As illustrated in FIG. 10, in the gel injection instrument introducing step S30a, the operator causes an introducer sheath 340 to dwell in a small wound 7 formed in the vicinity of the lesion area 1, and inserts the catheter 320 through the introducer sheath 340 to cause the catheter 320 to communicate with the lesion area 1. The lesion area 1 is similar to that previously described.

Figure 11:
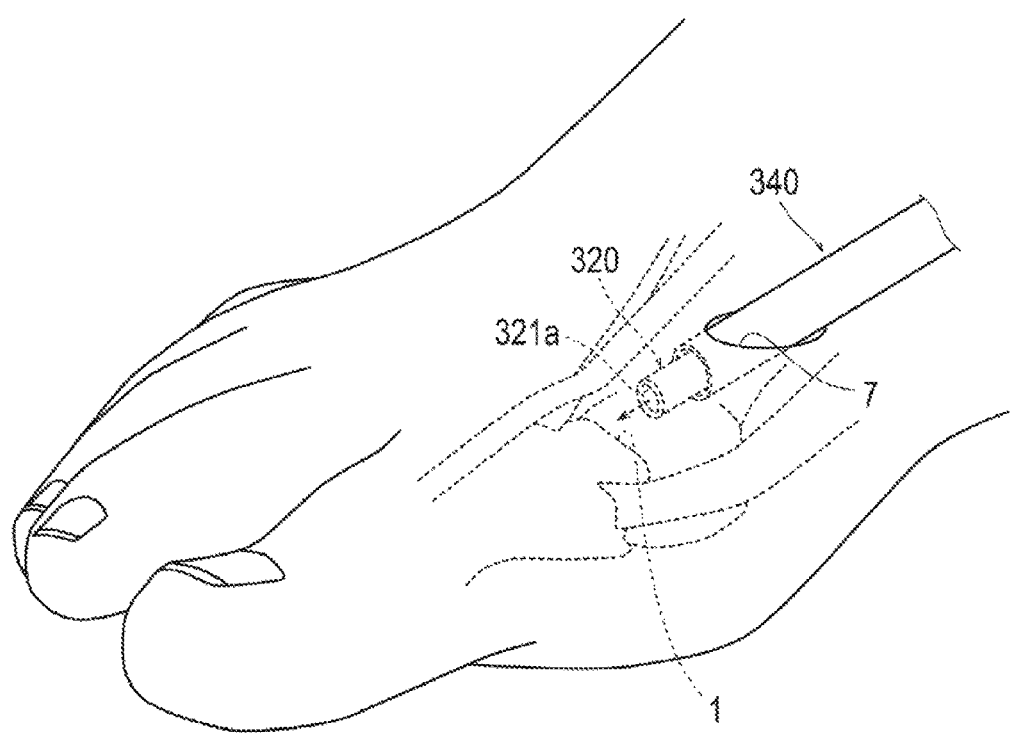
FIG. 11 is a diagram illustrating injection of a gel-like material through the catheter in accordance with an embodiment of the present disclosure.

As illustrated in FIG. 11, in the gel injection step S30b, the operator injects a gel-like material toward the lesion area 1 from the catheter 320, which is located to communicate with the lesion area 1. After injection of the gel-like material, the operator extracts the catheter 320 while causing the introducer sheath 340 to dwell, and then performs the instrument introducing step S31.

Figure 12:
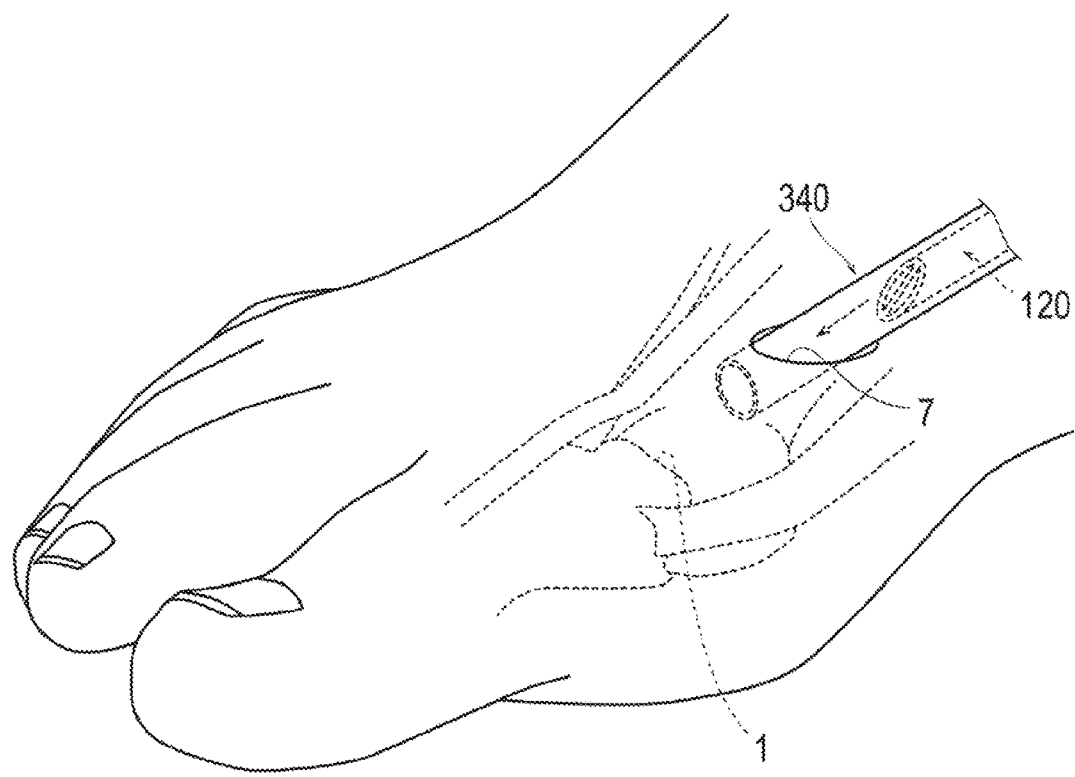
FIG. 12 is a diagram illustrating insertion of a puncture instrument into a wound in accordance with an embodiment of the present disclosure.

As illustrated in FIG. 12, in the instrument introducing step S31, the puncture instrument 120 is inserted through the introducer sheath 340, which is located to dwell in the wound 7, and is then caused to communicate with the lesion area 1. This eliminates the need for forming a new wound, thus enabling relieving the burden on the patient. Furthermore, since the puncture instrument 120 is guided by the introducer sheath 340, the puncture instrument 120 becomes easy to insert.

Figure 13:
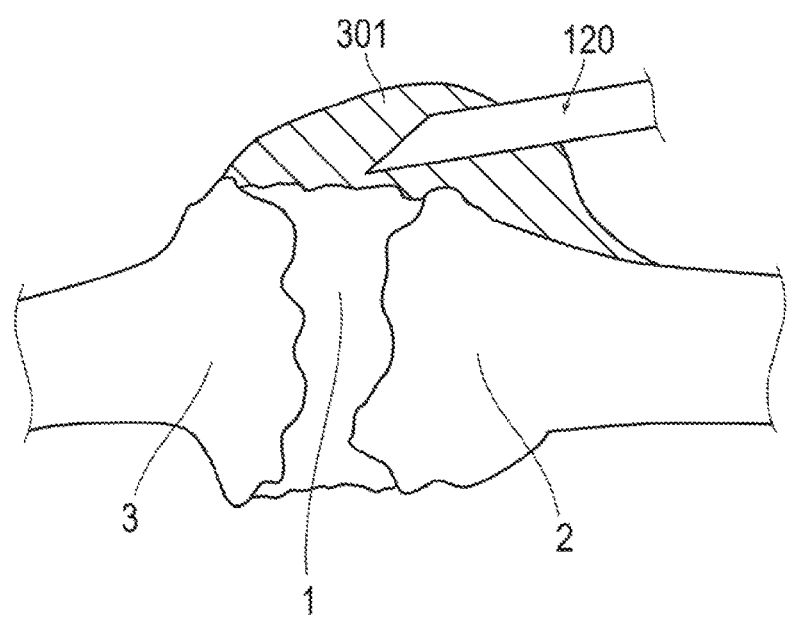
FIG. 13 is a diagram illustrating a condition in which the puncture instrument is inserted between the gel-like material and the lesion area in accordance with an embodiment of the present disclosure.

As illustrated in FIG. 13, as the gel-like material 301 has been injected in such a way as to cover the lesion area 1, in the instrument introducing step S31, the puncture instrument 120 is inserted between the gel-like material 301 and the lesion area 1. In that condition, the treatment step S32 is performed.

The treatment step S32 is the same as the treatment step S12 described above, in which the perfusion and discharge of the lavage fluid are carried out through a single puncture instrument 120, so that causative agents are removed from the lesion area 1. Then, the post-procedure step S33, which is similar to the post-procedure step S13 described above, is performed.

In some embodiments, the lesion area 1 may be covered with the gel-like material 301 and the perfusion and discharge of the lavage fluid can be carried out between them, and as such the lavage fluid is unlikely to spread from the lesion area 1 to other locations, so that the removal effectiveness for causative agents can be increased.

Furthermore, embodiments also include a structure similar to that previously described, and the function effect provided by such a structure may be similar to that previously described.

The present disclosure should not be construed to be limited to the above-described embodiments, but can be modified or altered in various manners within the claims.

For example, while, in the above-described embodiments, a single puncture instrument 120 and two catheters 220 and 230 are disclosed as examples of an instrument for performing the perfusion and discharge of a lavage fluid, the disclosure is not limited to such configurations. The disclosure also includes a configuration in which three or more instruments having a tubular shape are used to perform the perfusion and discharge of a lavage fluid.

Moreover, the gel supply unit 310 and the catheter 320 described above can be incorporated into the arthritis treatment system 200 described.

Furthermore, the therapeutic objective in the disclosure is not limited to gout, but can be any crystal-induced arthritis, a causative agent of which is a crystal depositing in the joint, such as pseudogout and basic calcium phosphate (BCP) crystal deposition disease.

Additionally, the lesion area is not limited to the one described in the above-described embodiments, but can be another joint in the foot different from the one described in the above-described embodiments and can also be a joint in regions other than the foot, such as the knee, lower back, shoulder, elbow, hand, and breast bone.

DESCRIPTION OF REFERENCE NUMERALS 1 lesion area,
2 first metatarsal bone,
3 proximal phalanx,
4, 5, 6, 7 wound,
100 arthritis treatment system,
110 lavage fluid supply unit,
120 puncture instrument (a single instrument having a tubular shape),
121 needle,
121a one lumen,
121b the other lumen,
122 main body portion,
123 first hub portion,
124 second hub portion,
200 arthritis treatment system,
210 aspiration unit,
220 catheter (one of two instruments having a tubular shape),
221 main body portion,
221a lumen,
223 hub portion,
230 catheter (the other of two instruments having a tubular shape),
231 main body portion,
231a lumen,
233 hub portion,
300 arthritis treatment system,
301 gel-like material,
310 gel supply unit,
320 catheter (an instrument having a tubular shape communicating with the gel supply unit),
321 main body portion,
321a lumen,
323 hub portion,
340 introducer sheath,
S11, S21, S31 instrument introducing step,
S12, S22, S32 treatment step,
S13, S23, S33 post-procedure step,
S30a gel injection instrument introducing step,
S30b gel injection step.

What is claimed is:

1. An arthritis treatment method comprising:
   a gel injection step of injecting a gel-like material toward a lesion area in which crystal-induced arthritis occurs, wherein the gel-like material covers the lesion area;
   an instrument introducing step of causing at least one instrument having a tubular shape to communicate with the lesion area, wherein the instrument is inserted between the gel-like material and the lesion area; and
   a treatment step of removing a causative agent of the crystal-induced arthritis from the lesion area by perfusion and discharge of a lavage fluid through the at least one instrument while the instrument is inserted between the gel-like material and the lesion area, and wherein the lavage fluid is prevented from spreading from the lesion area via the gel-like material covering the lesion area during the treatment step.

2. The arthritis treatment method according to claim 1, wherein, in the instrument introducing step, a single instrument of the at least one instrument is caused to communicate with the lesion area, and
   in the treatment step, the causative agent is removed by the perfusion and discharge through the single instrument.

3. The arthritis treatment method according to claim 1, wherein, in the instrument introducing step, two instruments of the at least one instrument are caused to communicate with the lesion area, and
   in the treatment step, the causative agent is removed by the perfusion through one of the two instruments and the discharge through the other of the two instruments.

4. The arthritis treatment method according to claim 1, wherein the method further comprises:
   causing an introducer sheath to dwell in a position adjacent to the lesion area prior to the gel injection step;

inserting a catheter into the introducer sheath, wherein the catheter injects the gel-like material covering the lesion area;

removing the catheter from the introducer sheath while the introducer sheath remains in the position adjacent to the lesion area; and wherein the instrument introducing step includes inserting the instrument into the introducer sheath while the introducer sheath remains in the position adjacent to the lesion area.

5. The arthritis treatment method according to claim 1, wherein the crystal-induced arthritis is gout.

\* \* \* \* \*